(12) United States Patent  
Bouduban et al.

(10) Patent No.: US 9,949,745 B2  
(45) Date of Patent: Apr. 24, 2018

(54) SYSTEMS, DEVICES, AND METHODS FOR GUIDING SURGICAL DEVICES INTO BONE

(71) Applicant: MEDOS INTERNATIONAL SARL, Le Locle (CH)

(72) Inventors: Nicolas Bouduban, Brugg (CH); Patrick Burki, Solothurn (CH)

(73) Assignee: MEDOS INTERNATIONAL SARL, Le Locle (CH)

( * ) Notice: Subject to any disclaimer, the term of this patent is extended or adjusted under 35 U.S.C. 154(b) by 750 days.

(21) Appl. No.: 14/339,577

(22) Filed: Jul. 24, 2014

(65) Prior Publication Data

US 2016/0022288 A1    Jan. 28, 2016

(51) Int. Cl.
*A61B 17/88* (2006.01)
*A61B 17/17* (2006.01)

(52) U.S. Cl.
CPC ...... *A61B 17/1739* (2013.01); *A61B 17/1728* (2013.01); *A61B 17/1778* (2016.11)

(58) Field of Classification Search
CPC ........ A61B 17/1684; A61B 2017/1778; A61B 17/1778
See application file for complete search history.

(56) References Cited

U.S. PATENT DOCUMENTS

| | | | |
|---|---|---|---|
| 5,250,055 A * | 10/1993 | Moore | A61B 17/0469 128/898 |
| 5,700,266 A | 12/1997 | Harryman, II | |
| 5,951,561 A | 9/1999 | Pepper et al. | |
| 6,352,538 B2 | 3/2002 | McGuire et al. | |
| 7,204,839 B2 | 4/2007 | Dreyfuss et al. | |
| 8,257,359 B2 | 9/2012 | Burkhart et al. | |
| 2007/0288031 A1 | 12/2007 | Dreyfuss et al. | |
| 2011/0015675 A1 * | 1/2011 | Howard | A61B 17/0401 606/232 |
| 2012/0123417 A1 | 5/2012 | Smith | |
| 2013/0023891 A1 * | 1/2013 | Berberich | A61B 17/1714 606/98 |

* cited by examiner

*Primary Examiner* — Matthew Lawson

(57) ABSTRACT

Devices, systems, and methods are generally provided for guiding surgical devices into a desired location and orientation in a bone. In general, the devices can include an elongate guide, a sleeve having an inner lumen therethrough for seating the guide, and a locking mechanism configured to lock a position of the guide with respect to the sleeve. The guide can have a distal, bone-engaging portion that can be laterally offset from an intermediate portion of the guide by a predetermined distance and that can extend distally beyond the sleeve to contact a bony structure. The guide can thus orient and stabilize the sleeve at the predetermined distance from the bony structure to provide for the delivery of one or more surgical devices through the sleeve and into the bone at a desired location and orientation, without requiring a surgeon to actually view the surgical site.

26 Claims, 7 Drawing Sheets

SYSTEMS, DEVICES, AND METHODS FOR GUIDING SURGICAL DEVICES INTO BONE

FIELD

The present disclosure relates to systems, devices, and methods for guiding one or more surgical devices to a desired location and orientation with respect to a bone.

BACKGROUND

Many surgical procedures involve placing an implant into bone. For example, when fixing a relationship between adjacent bones or bone segments, one common procedure involves driving one or more screws into the bone(s) to serve as an anchoring device for a fixation element, such as a relatively rigid fixation rod. The fixation element can have a predetermined contour that has been designed according to the properties of the target implantation site, and once installed, can hold the bones or bone segments in a desired spatial relationship until desired healing or fusion has taken place.

In many such procedures, the implant can be placed in the bone at a desired location and/or orientation by driving the implant into the bone. In some procedures, it may be necessary to place the implant into a location near the edge of the bone, for example where the bone has a small width or where the implant is being used to anchor the bone to an adjacent bone. However, it is often desirable to not drive an implant into a portion of a bone that is near the edge of the bone because the implant might cause the edge of the bone to fracture and/or the implant may skive off the edge of the bone. Inserting the implant into the desired position can be complicated by a variety of factors, e.g., the adjacent anatomy, the small size of the bone, irregularities in the shape of the bone, etc. In minimally invasive surgeries, which are becoming increasingly popular, the difficulties with accurately locating an appropriate location and orientation for an implant within the bone can be exacerbated. Traditionally, positional determination can be performed by imaging techniques such as X-rays, even during open surgery, but this can require temporary cessation of the procedure and may need to be performed multiple times throughout a single procedure, thereby increasing a risk related to the use of X-rays.

One particularly complex anatomy for inserting a bone implant is the shoulder joint, for example during a glenoid fixation procedure. During traditional glenoid fixation procedures, one or more bone screws are inserted into the shoulder blade adjacent to the glenoid rim. The glenoid rim can be small, difficult to access, and can have an irregular surface, making it difficult for surgeons to insert a screw into the glenoid rim at a location that is far enough away from the edge to prevent the screw from damaging the shoulder blade. Although this procedure is traditionally performed in open surgery, recently there has been a greater demand to provide for a minimally invasive form of glenoid fixation, which further complicates correct placement of the bone screw in the shoulder blade. Another procedure involving complex anatomies that complicate placement of bone implants is a bone block procedure, in which a bone graft is used to reconstruct a joint surface.

Accordingly, there is a need for devices, systems, and methods to facilitate guiding surgical devices such as a bone implant to a desired location and orientation in the bone.

SUMMARY

Systems, devices, and methods are generally provided for guiding surgical devices into a bone. In one exemplary embodiment, a surgical guide system is provided that includes a sleeve having an inner lumen extending therethrough, a guide that is removably insertable into the inner lumen of the sleeve, and a locking mechanism configured to maintain a location of the guide with respect to the sleeve in a fixed position in which a portion of the guide extends through the inner lumen and the distal tip extends distally beyond a distal-most end of the sleeve. The guide can have a distal tip that is laterally offset from a central longitudinal axis of the inner lumen by a predetermined distance, which, in some embodiments, can be in the range of about 3 millimeters to about 12 millimeters.

In some embodiments, the locking mechanism can include a trocar that is removably insertable into the inner lumen of the sleeve to engage the guide and maintain the guide in the fixed position. The trocar can include at least one guide passageway configured to receive the guide therein. The at least one guide passageway can have one or more walls configured to engage the guide to maintain the guide in the fixed position. The trocar can further include a K-wire passageway configured to slidably receive a K-wire that is configured to be inserted into bone. The K-wire passageway can extend through a cross-sectional center of the trocar and the at least one guide passageway can be disposed radially outward from a diameter of the K-wire passageway. Additionally or alternatively, the locking mechanism can include a slot formed in the guide and configured to engage the guide to maintain it in the fixed position.

The guide can have a proximal portion that comprises a stopper and that extends proximally beyond a proximal-most end of the sleeve when the guide is in the fixed position. In some embodiments, the guide can be made from a shape-memory material or flexible material. In still further embodiments, the sleeve can have at least one slot extending through a sidewall thereof, with the slot being configured to allow the guide to pass therethrough.

In another aspect, a wire guide is provided for providing a stabilizing offset for drilling a hole in bone. The wire guide can include a distal portion, an intermediate portion, and a proximal portion. The distal portion can be laterally offset from the intermediate portion by a predetermined distance and/or can have a shape that corresponds to a shape of an edge of a bone with which the guide is configured to be used to create a stabilizing offset. In this way, when the distal portion engages the bone, the wire guide establishes an offset position at which a hole is to be drilled in the bone engaged by the distal portion. The proximal portion can have a loop formed therein.

Further, the distal portion can be formed from a shape memory material and/or can have an S-shape. In some embodiments, the wire can be configured to be integrally formed with a sleeve having an inner lumen extending therethrough such that the distal portion of the wire extends distally beyond a distal-most end of the sleeve.

In another aspect, a surgical method is provided that includes inserting a sleeve through an opening in a patient's body and adjacent to a bone, passing a guide distally through an inner lumen of the sleeve until a distal tip of the guide extends distally beyond a distal-most end of the sleeve, rotating the guide such that its distal tip is disposed outside of a diameter of the sleeve, placing a guide placement surface of the guide distal tip against an edge of the bone such that the inner lumen of the sleeve is proximate to a bore formation location on the bone that is offset from the edge of the bone, and forming a bore in the bone at the bore formation location. In some embodiments, the bone is a scapula and the edge of the bone is the glenoid rim.

In some embodiments, the method can further include securing a fixed location of the guide with respect to the sleeve after the distal tip of the guide extends distally beyond the distal-most end of the sleeve. The securing can include inserting a trocar distally through the inner lumen. Further, the method can include inserting a K-wire distally through the trocar and into the bone and, in some embodiments, removing the guide and the trocar from the sleeve once the K-wire has been placed in the bone. Additionally or alternatively, the method can further include adjusting a location of the distal tip with respect to a main body of the guide after the guide has been passed distally through the sleeve.

The steps of the method can be performed in any order. For example, in some embodiments, the sleeve and the guide can be inserted into the patient's body simultaneously. In other embodiments, the sleeve can be inserted into the patient's body before the guide, while in still other embodiments the guide can be inserted into the patient's body before the sleeve.

BRIEF DESCRIPTION OF DRAWINGS

This invention will be more fully understood from the following detailed description taken in conjunction with the accompanying drawings, in which.

DETAILED DESCRIPTION

Figure 1:
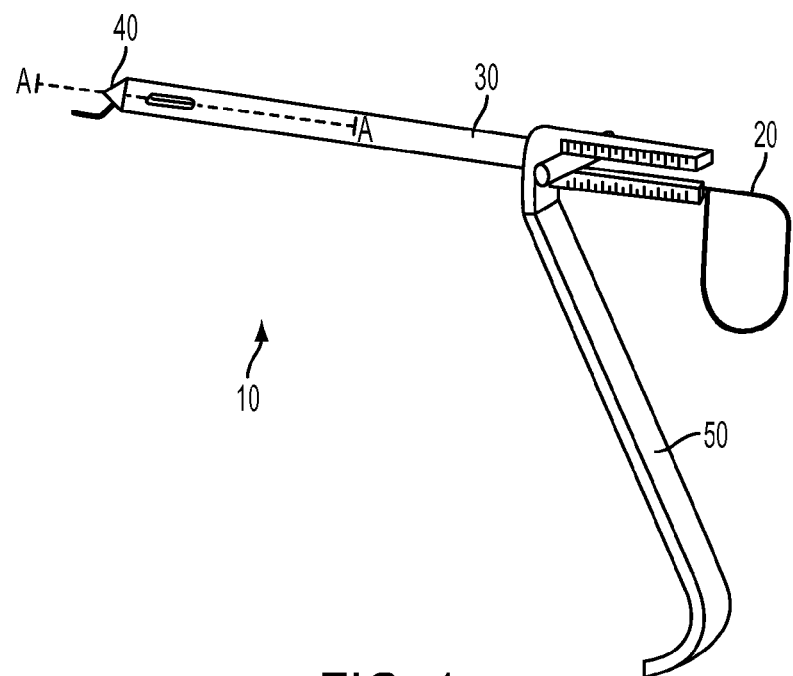
FIG. 1 is a perspective view of one embodiment of a guide system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In the present disclosure, like-numbered components of the embodiments generally have similar features and/or purposes. Further, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the size and shape of the components with which the systems and devices are being used, the anatomy of the patient, and the methods and procedures in which the systems and devices will be used. The figures provided herein are not necessarily to scale.

Devices, systems, and methods are generally provided for guiding surgical devices into a desired location and orientation in a bone. In general, the guide systems can include an elongate guide, a sleeve having an inner lumen therethrough for seating the guide, and a locking mechanism configured to lock the guide within the sleeve in a fixed position. The guide can have a distal, bone-engaging portion that can be laterally offset from an intermediate portion of the guide and a proximal portion that can be configured to indicate and/or to adjust a direction of the lateral offset. The guide can be configured to pass distally through the sleeve until the distal portion of the guide extends beyond a distal end of the sleeve, an intermediate portion of the guide extends through the sleeve, and the proximal portion of the guide extends proximally beyond a proximal end of the sleeve. When seated within the sleeve in this way, the distal portion of the guide can extend radially outward beyond an edge of the sleeve and the proximal portion of the guide can be manipulated by a user to orient the distal portion in a desired angular position, where the guide can be optionally locked in place by the locking mechanism. Thus positioned, the distal portion of the guide can contact a bony structure, for example an edge of the bone, to thereby brace the sleeve against the bony structure at a desired location and orientation. The guide can orient and stabilize the sleeve to provide for the delivery of one or more surgical devices through the sleeve and into the bone at the desired location and orientation, without requiring a surgeon to actually view the surgical site. The guide can thus be useful for arthroscopic surgery, where surgical devices must pass through small openings and around complex anatomy, by providing a large lateral offset for the guide with a small diameter sleeve. Where the bone is fractured, the guide can help to hold pieces of the bone together prior to and during fixation.

One exemplary embodiment of a system 10 for orienting one or more surgical devices with respect to a bone is illustrated in FIG. 1. The system 10 can include a guide 20, a sleeve 30, and a locking mechanism, as shown a trocar 40. When the system 10 is assembled, the guide 20 can be configured to extend through a passageway 43 of the trocar 40, which in turn can be configured to extend through a lumen 32 of the sleeve 30. The trocar 40 can be configured to lock the guide 20 in place within the sleeve 30, such that the guide 20 can orient the sleeve 30 and any devices passed therethrough at a desired distance and orientation from a bony structure that is contacted by the guide 20. While the illustrated embodiment provides for the trocar 40 as the locking mechanism, it will be appreciated by a person skilled in the art that a variety of other locking mechanisms can be used to set a location of the guide 20 with respect to the sleeve 30. Further, in some embodiments the locking mechanism can be integrated with the sleeve 30 such that the system 10 only includes the guide 20 and the sleeve 30. It will further be appreciated that the use of multiple components for orienting one or more surgical devices, including the guide 20, the sleeve 30, and optionally the trocar 40, can enhance the flexibility of the surgical system 10 by providing the option of only using only a subset of the components. Further, as will be explained in detail below, the use of the sleeve 30 together with the guide 20 can facilitate delivery of the guide 20 through a small surgical incision while still providing for a large lateral offset between a location of a bone implant and a bony structure contacted by the guide 20.

Figure 2:
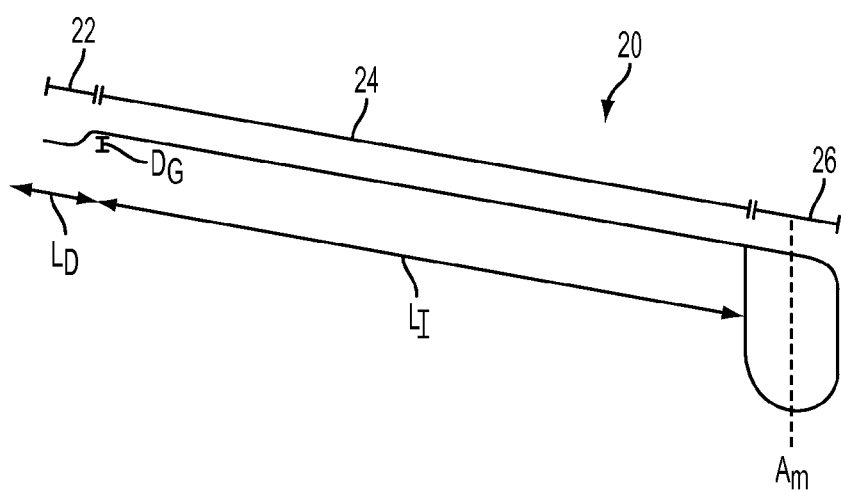
FIG. 2 is a side view of a guide from the guide system of FIG. 1.

As shown in FIG. 2, the guide 20 can be an elongate body, e.g., a wire, that can include a distal portion 22, a proximal portion 26, and an intermediate portion 24 extending therebetween. The distal portion 22 can be any shape and size that facilitates engagement of the distal portion 22 with a bony structure while preventing injury of the bone and/or surrounding tissue. For example, the distal portion 22 can be formed from a semi-rigid material to facilitate passage of the guide 20 into a surgical site, and/or the distal end 22 can have a blunt distal tip to help prevent injury to tissue, e.g., cartilage, at the surgical site. In the illustrated embodiment, the distal portion 22 forms a flat surface that is offset from and substantially parallel to the intermediate portion 24. In this way, the distal portion 22 forms an S-shape with respect to the intermediate portion 24. Because the distal portion 22 of the illustrated embodiment is substantially flat, it can help to align the guide 20 with a substantially flat portion of the bone. However, it will be appreciated by a person of skill in the art that the shape of the distal portion 22 can be customized for use with a particular bony structure and/or with an individual patient's bone. For example, the shape of the distal portion 22 can be molded based on an image of a patient's bone structure.

To facilitate delivery of one or more surgical devices at a predetermined distance from the bony structure, at least a part of the distal portion 22 can be laterally offset from the intermediate portion 24 by a predetermined distance $D_G$. The distance $D_G$ can vary according to a patient's anatomy (e.g., child versus adult and/or male versus female) and/or to a desired offset of the one or more surgical devices from the bony structure. In general, the distance $D_G$ can be optimized to allow for the placement of a surgical device far enough away from the bony structure, e.g., the edge of the bone, to prevent the device from passing through, falling out, or skiving off the bone. When used in glenoid fixation procedures, the distance $D_G$ can be in a range of about 3 millimeters to about 6 millimeters to facilitate placement of a bone screw about 3 millimeters to about 6 millimeters away from the glenoid rim. Similarly, a length $L_D$ of the distal portion 22 can be sized to allow for the guide 20 to extend beyond a distal end of the sleeve 30 to reach a bony structure. In general, the length $L_D$ can be in a range of about 3 millimeters to about 30 millimeters.

To facilitate delivery of the one or more surgical devices in a desired angular orientation with respect to the bony structure, the distal portion 22 can be bent to the desired angular orientation with respect to the intermediate portion 24. In this way, where the intermediate portion 24 is seated within the sleeve 30 and the distal portion 22 abuts the bony structure, the guide 20 can orient the sleeve 30 at the desired angular orientation with respect to the bony structure. Devices passing through the sleeve 30 along a track that is parallel to a longitudinal axis L of the sleeve 30 can thus be oriented at the desired angular position with respect to the bone. Using the illustrated embodiment of FIGS. 1-2 as an example, the S-shape of the guide 20 can be used to orient surgical devices passing through the sleeve 30 in a substantially parallel orientation with respect to a bony structure, e.g., the edge of a bone. Specifically, the distal portion 22 can abut a substantially flat portion of the edge of the bone, and the intermediate portion 24 can be aligned along the longitudinal axis L of the sleeve 30. In this way, the sleeve 30 can be oriented substantially parallel to the edge of the bone and devices passing through the sleeve 30 can also be oriented substantially parallel to the edge of the bone. The parallel alignment of surgical devices with the edge of the bone can be particularly advantageous for, e.g., inserting a bone screw into the bone in close proximity to the edge of the bone such that the screw does not pass through the bone or skive off the bone. It will be appreciated by a person of skill in the art that the distal and intermediate portions 22, 24 can be oriented at any angular position with respect to one another to achieve any desired angular orientation of surgical devices with respect to a bony structure.

Figure 3:
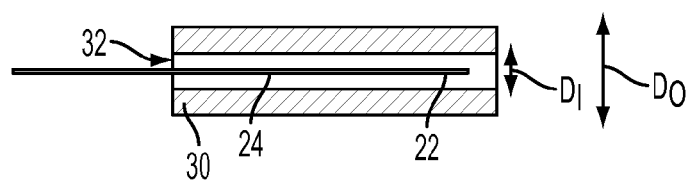
FIG. 3 is a cross-sectional view of a guide and sleeve of the guide system of FIG. 1 taken along the line A-A, the guide being in a compressed configuration.
Figure 4:
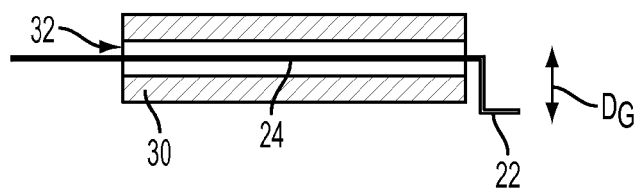
FIG. 4 is a cross-sectional view of the guide and sleeve of FIG. 3, the guide being in an expanded configuration.

To facilitate insertion of the guide 20 into a surgical site, in some embodiments the distal portion 22 can be configured to move between an expanded configuration, in which an effective width of the guide 20 is large, and a compressed configuration, in which an effective width of the guide 20 is small. For example, as illustrated in FIGS. 3-4, the distal portion 22 can be biased to the expanded configuration and capable of being moved to the compressed configuration when acted upon by an external force. In this way, the distal portion 22 can be configured to have a small width when passing through the sleeve 30 or other cannulated device, but to have a larger width once it passes out the distal end of the sleeve 30 or other cannulated device. In the illustrated embodiment, the distal portion 22 can be biased to the S-shape in the expanded configuration, with the distal portion 22 being laterally offset from the intermediate portion 24 by the first predetermined distance $D_G$ (FIG. 4). When disposed within the sleeve 30, the distal portion 22 can move to the compressed configuration in which the distal portion 22 extends substantially parallel to the intermediate portion 24 in a straight line (FIG. 3). Thus, in the expanded configuration, the guide 20 can have an effective width $D_G$, but in the compressed configuration, the guide 20 can have an effective width equal to a diameter of the guide 20.

The intermediate portion 24 of the guide 20 extends between the proximal and distal portions 26, 22 and can be configured to be at least partially seated within the lumen 32 of the sleeve 30. In the illustrated embodiment, the intermediate portion 24 is substantially straight and has a length $L_I$ that is substantially equal to a length $L_S$ of the sleeve 30, such that the entire intermediate portion 24 can be enclosed within the lumen 32 of the sleeve 30. However, the length $L_I$ can be less than the length $L_S$, to allow for at least a part of the intermediate portion 24 to extend proximally and/or distally of the sleeve 30.

The proximal portion 26 can be configured indicate an orientation of the distal portion 22 and/or to change the orientation of the distal portion 22, which can be useful when the distal portion 22 is inserted through an incision into the patient's body and is not visible to the user. In the illustrated embodiment, the proximal portion 26 is shaped as a loop having a major axis $A_M$ that is parallel to a direction of offset of the distal portion 22 from the intermediate portion 24. Further, the loop is formed on the same side of the guide 20 as the distal portion 22. Thus, the user can know the direction of offset of the distal portion 22 by observing the direction of offset of the loop formed by the proximal portion 26, which corresponds to the offset of the distal portion 22. In this way, where the proximal portion 26 is disposed externally of a patient's body, the user can know the direction of the lateral offset of the distal portion 22 within the patient's body without being able to see the distal portion 22. This feature can be particularly useful for minimally invasive surgical procedures, in which the guide 20 is inserted through a portal to minimize trauma incurred by the surgery. It will be appreciated by a person skilled in the art that the proximal portion 26 can include any direction indication feature, such as an etching or marking on an exterior surface of the proximal portion 26.

The proximal portion 26 can be configured for gripping by a user to help manipulate the guide 20, particularly where the proximal portion 26 is configured to change an orientation of the distal portion 22. In the illustrated embodiment, the user can insert one or more fingers through the loop formed by the proximal portion 26 to grip the proximal portion 26 between the user's one or more fingers and, e.g., the user's thumb. In some embodiments, the proximal portion 26 can serve as a stop to prevent passage of the guide 20 into a patient's body beyond a desired distance. In the illustrated embodiment, for example, a diameter of the loop is large enough to prevent distal advancement of the guide 20 through the sleeve 30 when the loop abuts a proximal end of the sleeve 30.

The guide 20 can be formed from any one or more materials that are suitable for insertion into the patient's body. In some embodiments, the distal, intermediate, and proximal portions 22, 24, 26 can be made from different materials than one another and/or can be made from different materials along a length thereof. For example, in some embodiments, at least the distal portion 22 can be formed from a shape memory material, which can include a single material or any combination of materials, to cause the distal portion 22 to be laterally biased away from the intermediate portion 24 and/or to assume a shape that facilitates engagement with bone. In other words, the distal portion 22 can flare away from the intermediate portion 24 in the expanded configuration. Non-limiting examples of shape memory materials include copper-zinc-aluminum-nickel alloys, copper-aluminum-nickel alloys, nickel-titanium alloys such as Nitinol, thermoplastic materials such as Nylon or Nylon blends, and shape memory polymers such as Veriflex™. The shape memory material can facilitate advancement of the guide 20 into tissue by allowing for at least the distal portion 22 of the guide 20 to be deformed or bent into the compressed configuration in which the guide 20 has a smaller width than a width thereof in the expanded configuration, while also allowing the distal portion 22 of the guide 20 to automatically move from the compressed configuration to the expanded configuration. It will be appreciated by a person skilled in the art that any portion of the guide 20, including the entire guide 20, can be made from one or more shape memory materials.

In some embodiments the intermediate portion 24 can be made from any one or more materials that are less flexible than the proximal portion 26, and/or can be formed to have a hardness gradient that increases from a distal end to a proximal end thereof. In other embodiments, the distal portion 22 can be formed from one or more materials configured to avoid damage to soft tissue surrounding the target bone to be contacted by the distal portion 22. For example, the distal portion 22 can be formed from one or more flexible materials and/or can be formed from one or more smooth materials without sharp edges. By way of non-limiting examples, the guide 20 can be made from one or more materials including Nitinol, Gum Metal, spring steel, stainless steel, Titanium and polymers.

It will be appreciated by a person skilled in the art that the guide 20 can comprise only the distal portion 22 or only the distal and intermediate portions 22, 24. Also, in some embodiments, at least a portion of the guide 20 can be integrally formed with or permanently attached to the sleeve 30. For example, the guide can comprise only the distal portion 22. In such embodiments, the guide can be integrally formed with the distal end of the sleeve 30 such that it always extends distally beyond the sleeve 30, or it can be configured to be selectively extended distally beyond the sleeve 30 and retracted proximally into the sleeve 30, e.g., by an actuation mechanism located on a proximal portion of the sleeve 30. In either aspect, the guide is thus inherently locked in a fixed radial orientation with respect to the sleeve 30. Thus, a direction of the guide can be indicated by any indication feature, e.g., an arrow, etched onto the proximal portion of the sleeve 30.

Figure 5:
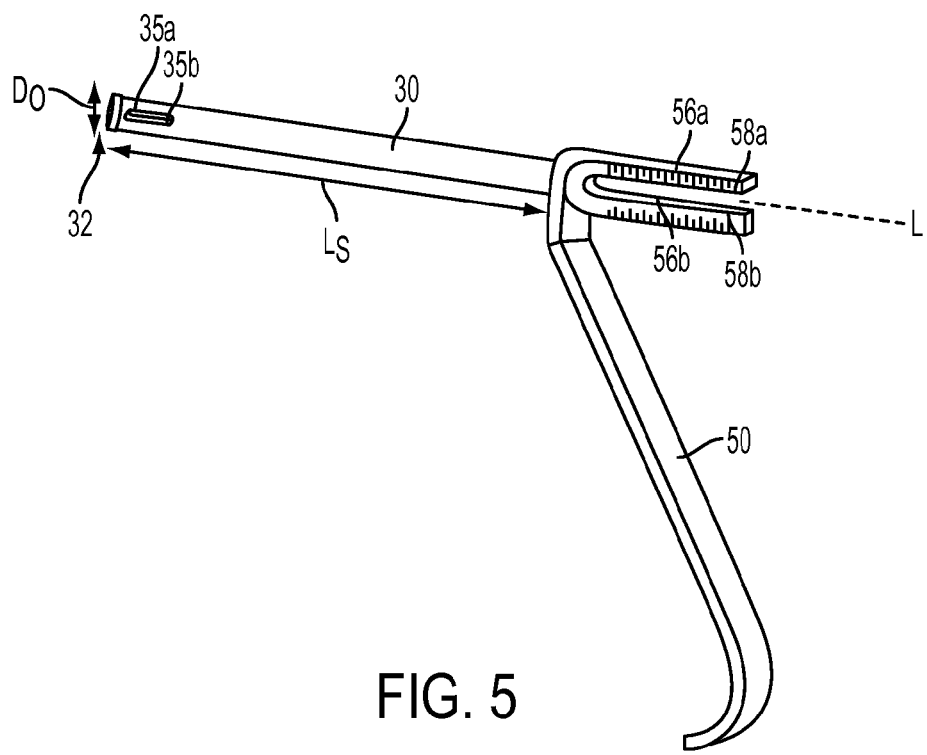
FIG. 5 is a perspective view of a sleeve and a handle from the guide system of FIG. 1.

The sleeve 30 can have a variety of sizes, shapes, and configurations. Generally, the sleeve 30 can be configured to be inserted at least partially into a body of a patient. By way of non-limiting example, the sleeve 30 can have a small outer diameter $D_o$ to facilitate insertion of the sleeve 30 into a patient's body, particularly during minimally invasive procedures and/or with complex anatomies. As shown in FIG. 5, the sleeve 30 has a cylindrical shape, but the sleeve 30 can have any other shape and a variety of outer diameters along the longitudinal length thereof. At least a distal portion of the sleeve 30 can be constructed of one or more substantially rigid materials to facilitate insertion into a patient, although a portion of the sleeve 30, e.g., a proximal portion, can be flexible. In some embodiments, the sleeve 30 can have one or more features thereon to facilitate endoscopic viewing of a surgical procedure. In the illustrated embodiment, the sleeve 30 has opposed cutouts 35a, 35b adjacent to the distal end of the sleeve 30 to serve as a viewing window for an endoscope passed through the sleeve 30.

An inner lumen 32 can extend along an entire longitudinal length L of the sleeve 30 such that the shaft 34 has a cannulated interior. The lumen 32 can be configured to facilitate the passage and/or use of surgical devices inserted into a patient's body therethrough, e.g., a cross-section of the lumen 32 can be shaped and sized to accommodate axial sliding of one or more surgical devices therethrough. For example, the lumen 32 can have an inner diameter $D_I$ that is large enough to allow for the guide 20 to pass therethrough.

Where the guide 20 is capable of moving between compressed and expanded configurations, the diameter $D_I$ can be small enough to compress the distal portion 22 of the guide 20 into the compressed configuration as the distal portion 22 passes through the sleeve 30, as shown in FIG. 4. In some embodiments, the lumen 32 can be large enough to seat the trocar 40 therein such that the trocar 40 can slide axially within the lumen 32. The lumen 32 in the illustrated embodiment has a cylindrical shape and only one inner diameter $D_I$, but the lumen 32 can have any other shape and varying diameters along a length thereof to accommodate one or more locking mechanisms for holding the guide 20 in place with respect to the sleeve 30.

In some embodiments, a handle 50 can be attached to a proximal end of the sleeve 30 to facilitate insertion of the sleeve 30 into a patient's body. The handle 50 can be attached to the sleeve 30 either permanently, for instance by being integrally formed with the sleeve 30, or it can be removably attached to the sleeve 30. The handle 50 can be configured in a variety of ways to improve the user's ability to deliver and/or position one or more surgical devices through the sleeve 30. For example, the handle 50 can have various features thereon to facilitate gripping, at least along the proximal portion thereof (e.g., ribs, protrusions, etc.), and/or can be formed from one or more materials that facilitate gripping. In the illustrated embodiment, the handle 50 is formed to provide for a pistol grip, although it will be appreciated by a person skilled in the art that the handle 50 can be any shape that facilitates gripping, e.g., a loop, a bulb, etc. In some embodiments, the handle 50 can be specially designed for ergonomic gripping.

To further facilitate delivery of one or more surgical devices through the sleeve 30, a portion of the handle 50 can have at least one depth indication feature formed thereon that provides information about a depth of devices inserted through the sleeve 30, which can be particularly useful in minimally invasive procedures where a distal portion of a device is inserted into the patient's body is not visible to the user. For example, sets of demarcation lines 56a, 56b extending proximally beyond the shaft 30 along arms 58a, 58b of the handle 50 can indicate a distance that a device has traveled into a surgical site. Although there are two sets of demarcation lines 56a, 56b in the illustrated embodiment to indicate distance in, e.g., two different units of measurement, there can be any number of sets of demarcation lines.

Figure 6A:
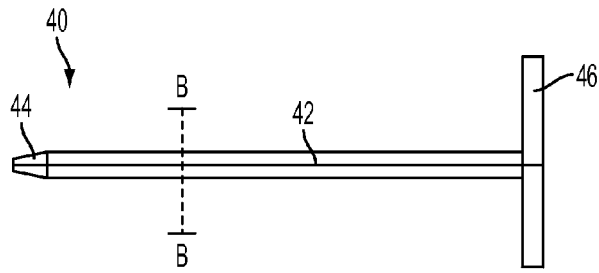
FIG. 6A is a side view of a trocar from the system of FIG. 1.
Figure 6B:
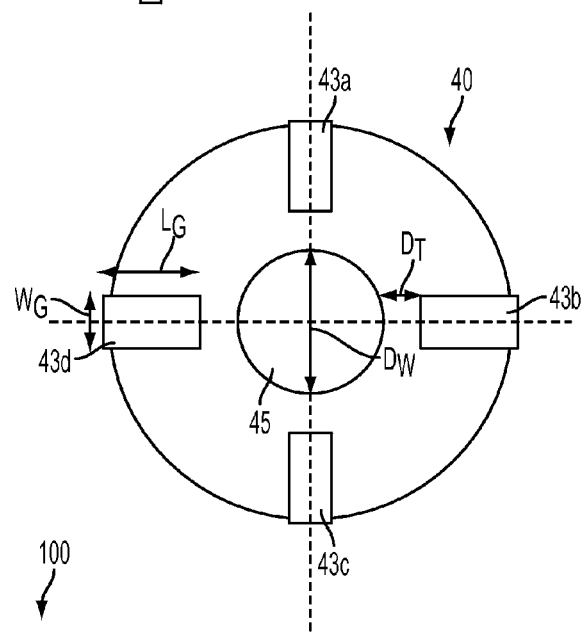
FIG. 6B is a cross-sectional view of the trocar of FIG. 6A taken from line B-B.

The surgical system 10 can include one or more locking mechanisms to lock a position of the guide 20 (e.g., an angular and/or axial position) with respect to the sleeve 30. The locking mechanism can be removably or permanently attachable to the sleeve 30, or it can be an integrally formed feature of the sleeve 30. In the illustrated embodiment, the locking mechanism is a trocar 40 that can be inserted into the inner lumen 32 of the sleeve 30. As shown in FIGS. 6A and 6B, the trocar 40 can include an elongate shaft 42, a substantially pointed distal region 44 and a handle 46. The pointed distal region 44 can be configured to extend distally beyond the distal end of the shaft 30 when the trocar 40 is inserted fully into the shaft 30 to facilitate insertion of the system 10 into a surgical site. The handle 46 can have any size and shape configured to assist a user in gripping the trocar 40 and inserting the trocar 40 into a surgical site. The handle 46 of the illustrated embodiment is an elongate member that is configured to extend through a gap between arms 54a, 54b of the handle 50. In this way, the handle 46 can serve as an indicator of a depth that the trocar 40 has been inserted into a surgical site and/or can serve as a stop to prevent the trocar 40 from being inserted further distally into the sleeve 30 once the handle 46 abuts the proximal end of the sleeve 30.

The trocar 40 can have one or more passageways extending therethrough for one or more surgical devices therein. The one or more passageways can extend through any cross-sectional portion and along any length of the trocar 40. As shown in FIG. 6B, the trocar 40 includes first, second, third, and fourth radial passageways 43a, 43b, 43c, and 43d, as well as a central passageway 45. Each of the passageways 43a, 43b, 43c, 43d, and 45 can have dimensions and a cross-sectional shape that is configured to slidably seat and/or to lock one or more surgical devices therein. For example, in the illustrated embodiment, the central passageway 45 has a diameter $D_W$ that is larger than a diameter of a device intended to be inserted only temporary into the bone, e.g., a K-wire, such that the K-wire can slide freely in and out of the passageway 45. This can be particularly useful where, for example, the K-wire is inserted into a hole in the bone to serve as a guide for a bone screw and is removed before insertion of the bone screw. However, it will be appreciated by a person skilled in the art that the passageway 45 can have any dimension corresponding to any surgical device configured to be inserted therethrough.

The passageways 43a, 43b, 43c, 43d, and 45 can be configured to engage a surgical device seated therein a variety of ways. In some embodiments, the dimensions of the passageway can be only slightly larger than corresponding dimensions of a surgical device to fix the device therein by interference fit while still allowing the device to slide within the passageway when acted on by an external force that exceeds a threshold force. In the illustrated embodiment, each of the radial passageways 43a, 43b, 43c, and 43d has a width $W_G$ and a length $L_G$ that are only slightly larger than the corresponding dimensions of a guide, e.g., the guide 20, to thereby create an interference fit with the guide 20 while allowing for axial sliding of the guide 20 when acted on by an external force that exceeds a threshold force. Additionally or alternatively, walls of the passageways 43a, 43b, 43c, and 43d can have gripping features to facilitate locking of the guide therein. By way of non-limiting example, the passageways 43a, 43b, 43c, and 43d can have one or more features to prevent rotation of the guide 20, e.g., the passageways 43a, 43b, 43c, and 43d can have one or more axial ridges protruding inwardly therefrom that align with corresponding channels extending axially along an exterior surface of the guide 20.

There can be any number of passageways extending through the trocar 40 for seating any number, size, and shape of surgical devices therethrough. As shown in FIG. 6B, the radial passageways 43a, 43b, 43c, and 43d are disposed radially of the central passageway 45, at right angles to one another. It will be appreciated by a person skilled in the art that the radial passageways 43a, 43b, 43c, and 43d can be arranged at any angle with respect to one another, to thereby allow for a guide passing therethrough to contact a target bone. The location of the radial passageways 43a, 43b, 43c, and 43d adjacent to an external rim of the trocar 40 can help to increase a lateral offset of the distal portion 22 of the guide 20 from a target location in the bone by a distance $D_T$, which is the distance between the central passageway 45 and each of the radial passageways 43a, 43b, 43c, and 43d. Specifically, a surgical device inserted through the central passageway 45 can be disposed at a distance $D_T D_G$ away from the bony structure that is contacted by the distal portion 22 of the guide. The distance $D_T$ can be adjusted to achieve the desired offset, and can be either the same or different for each of the radial passageways 43a, 43b, 43c, and 43d. Similarly, the relationship between $D_G$ and $D_T$ can vary and can be customized for a particular surgical procedure and/or to achieve a desired offset. By way of non-limiting example, where the procedure allows for a large diameter sleeve 30, the distance $D_T$ can be larger than the distance $D_G$. In general, the distance $D_T$ can be in a range of about 0.5 millimeters to about 20 millimeters.

It will be appreciated by a person of skill in the art that any number and type of locking mechanisms can be used to fix the guide 20 in place within the sleeve 30. By way of non-limiting example, the locking mechanism can include a ridge or protrusion extending inwardly from a wall of the lumen 32 of the sleeve 30. A recess corresponding in size and shape to the ridge or protrusion can be formed in the intermediate portion 24 of the guide 20, such that engagement between the ridge or protrusion and the corresponding recess serves to lock the guide 20 in place within the sleeve 30 at a fixed axial and/or angular position. It will be further appreciated by a person of skill in the art that the location of the protrusion or ridge and the recess can be reversed, such that the lumen 32 has a recess formed therein and the guide 20 has a protrusion or ridge formed thereon. Other mechanisms or features for setting the location of one component with respect to another can also be incorporated into the system 10 to facilitate locking a location of the guide 20 with respect to the sleeve 30. By way of non-limiting examples, a locking mechanism can include various male and female members incorporated into the guide 20 and sleeve 30 or an outside component configured to set a location of the guide 20 with respect to the sleeve 30, e.g., a compression component, clamp, nut, etc.

Figure 7A:
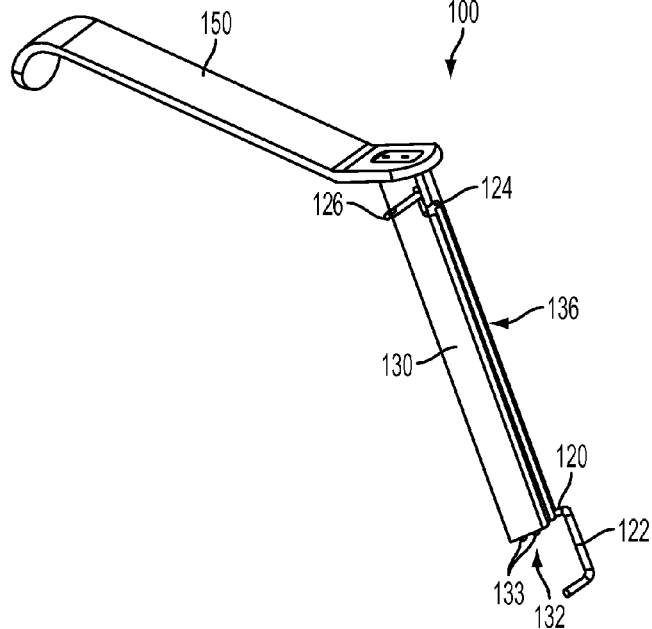
FIG. 7A is a perspective view of another embodiment of a guide system.
Figure 7B:
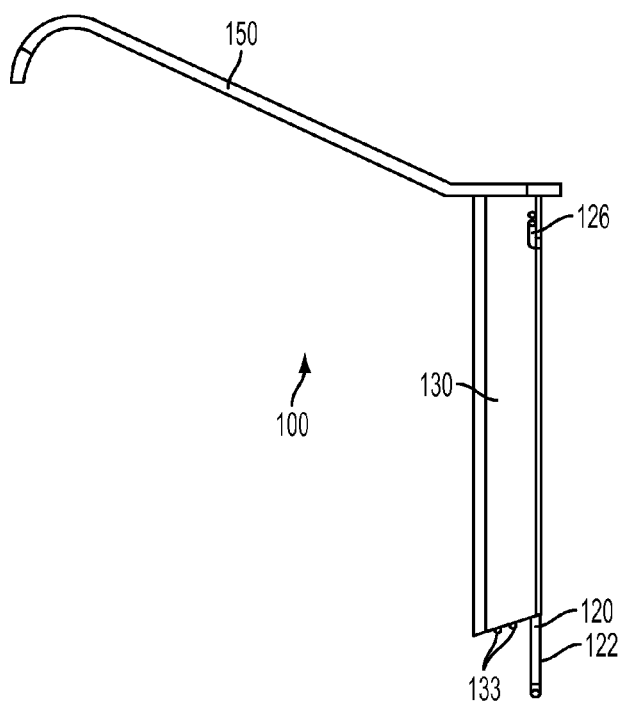
FIG. 7B is a side view of the guide system of FIG. 7A.
Figure 7C:
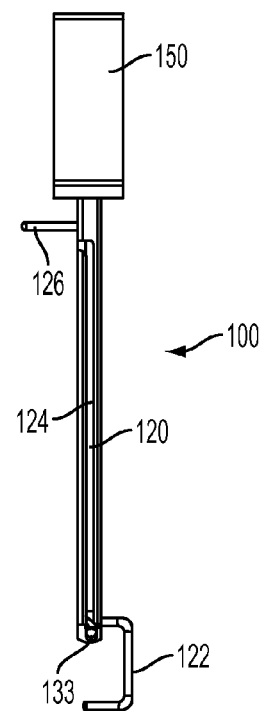
FIG. 7C is a front view of the guide system of FIG. 7A.
Figure 8A:
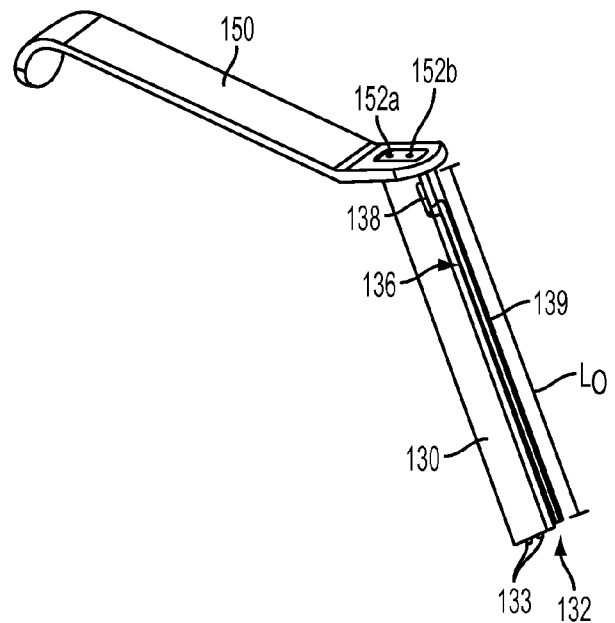
FIG. 8A is a perspective view of a sleeve and a handle of the guide system of FIG. 7A.
Figure 8B:
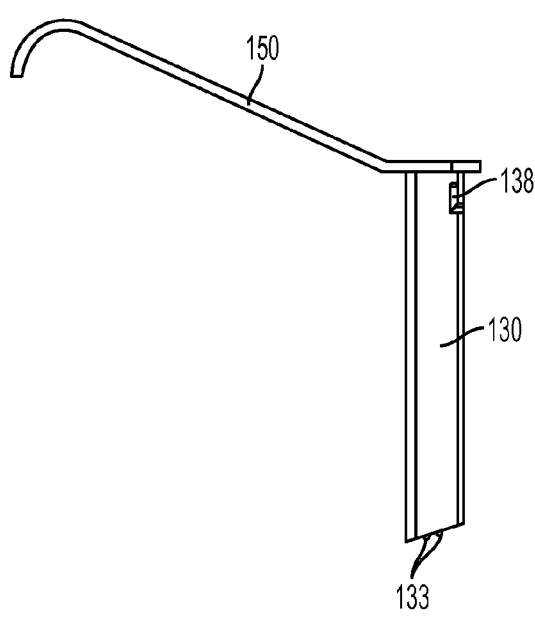
FIG. 8B is a side view of the sleeve and the handle of FIG. 8A.
Figure 8C:
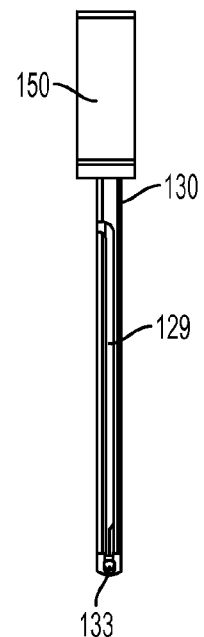
FIG. 8C is a front view of the sleeve and the handle of FIG. 8A.
Figure 9A:
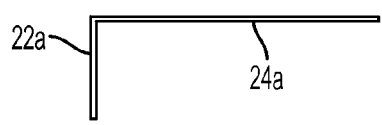
FIG. 9A is a side view of a distal end of an alternate embodiment of a guide.
Figure 9B:
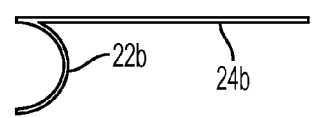
FIG. 9B is a side view of a distal end of another alternate embodiment of a guide.
Figure 9C:
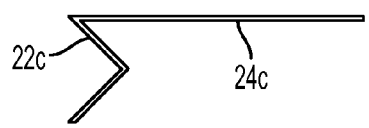
FIG. 9C is a side view of a distal end of another alternate embodiment of a guide.
Figure 9D:
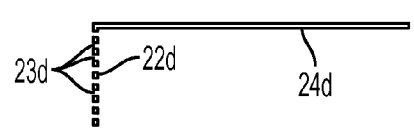
FIG. 9D is a side view of a distal end of another alternate embodiment of a guide.
Figure 9E:
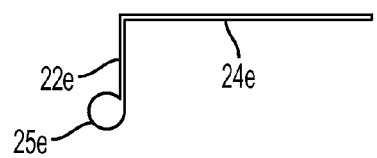
FIG. 9E is a side view of a distal end of another alternate embodiment of a guide.
Figure 9F:
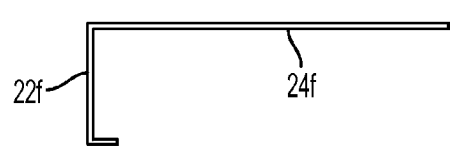
FIG. 9F is a side view of a distal end of another alternate embodiment of a guide.

Another exemplary embodiment of a system 100 for orienting one or more surgical devices with respect to a bone is illustrated in FIGS. 7A-8C, with FIGS. 7A-7C illustrating the assembled system 100 and FIGS. 8A-8C illustrating portions of the system, including a slotted sleeve 130 and an optional handle 150. The system 100 can include the slotted sleeve 130 and a guide 120 that is configured to be inserted at least partially into a lumen 132 of the sleeve 130 such that a distal, bone-engaging portion 122 of the guide 120 extends distally beyond a distal end of the sleeve 130. Thus positioned, the guide 120 can be configured to orient the sleeve 130 and any devices passed therethrough at a desired distance and orientation from a bony structure that is contacted by the distal portion 122 of the guide 120. At least an intermediate portion 124 of the guide 120 can be configured to be inserted into the lumen 132 through a longitudinal slot 136 in a sidewall of the sleeve 130. In this way, a distal, bone-engaging portion 122 of the guide 120 need not pass through the sleeve 130 in order for the system 100 to be assembled as shown in FIGS. 7A-7C. This side-loading capacity of the sleeve 130 can be particularly useful where, for example, the distal portion 122 of the guide 120 is too large to be passed through the sleeve 130.

Similar to the distal portion 22 of the guide 20, the distal portion 122 of the guide 120 can be laterally offset from an intermediate portion 124 of the guide 120 by a predetermined distance to help provide a stabilizing offset from a bony structure contacted by the distal portion 122. As shown in FIGS. 7A and 7C, the distal portion 122 is formed in a C-shape, which can enable the distal portion 122 to contact surfaces of the bony structure that are on an opposite side of the bony structure from a surface that is being operated on. In this way, the guide 120 can more effectively grasp the bony structure and can thereby enhance the stability of the guide system 100.

Similar to the proximal portion 26 of the guide 20, the proximal portion 126 of the guide 120 can have one or more direction indication features to indicate a direction of lateral offset of the distal portion 122. As best shown in FIG. 7C, the proximal portion 126 is bent in an opposite direction from the lateral offset of the distal portion 122, such that a user viewing the proximal portion 126 can know that the distal portion 122 is bent in an opposite direction when the distal portion 122 is disposed within a patient's body or is not otherwise visible. Further, in some embodiments, the proximal portion 126 can be manipulated to change an orientation of the distal portion 122. In the illustrated embodiment, the proximal portion 126 can be bent away from the intermediate portion 124 to facilitate gripping of the proximal portion 126. When the intermediate portion 124 of the guide 120 is seated in the lumen 132, the proximal portion 126 can thus extend outside the slot 136 and can be gripped by a user to manipulate the guide 120. Although the proximal portion 126 is bent away from the intermediate portion 124 by approximately ninety degrees in the illustrated embodiment, it will be appreciated by a person skilled in the art that the proximal portion 126 can extend at any angle to the intermediate portion 124, and can have any one or more features to facilitate gripping.

Like the sleeve 30, the sleeve 130 can generally be configured to be inserted at least partially into a body of a patient. Accordingly, the sleeve 130 can have one or more features thereon to facilitate insertion into the patient's body, e.g., teeth 133, on a distal end thereof to help pierce tissue. In some embodiments, at least a proximal portion of the sleeve 130 can be configured to remain outside the patient's body to thereby allow for manipulation of one or more surgical devices seated therein, as described in more detail below.

The sleeve 130 can have one or more slots, e.g., the slot 136, which can be configured to allow for side-loading of one or more surgical devices therethrough. In the illustrated embodiment, shown in FIGS. 8A-8C, the slot 136 is configured to allow for side-loading of the guide 120, and therefore has dimensions that are slightly larger than corresponding dimensions of the guide 120. In particular, the slot 136 has a length $L_O$ that is larger than a length of the intermediate portion 124 of the guide 120. However, it will be appreciated that the slot 136 can have any length suitable for passing any portion of the guide 120 therethrough. It will be further appreciated by a person skilled in the art that the slot 136 can be of any size and shape to facilitate the insertion and/or subsequent manipulation of a particular medical device, and that the sleeve 130 can have any number of slots formed therein, either the same or different from one another.

In some embodiments, the slot 136 can be configured to orient the distal portion 122 of the guide 120 in a desired manner when the intermediate portion 124 of the guide 120 is seated within the lumen 132 of the sleeve 130. Where the proximal portion 126 of the guide is configured to extend outwardly through the slot 136, for example, the location of the slot 136 can determine the orientation of the distal portion 122. Specifically, the distal portion 122 of the guide 120 can extend radially outwardly from a sidewall of the sleeve 130 that is opposite to the sidewall on which the slot 136 is formed. In still further embodiments, the slot 136 can be configured to orient the guide 120 in more than one orientation. As shown in FIGS. 8A-8C, at least a proximal portion 138 of the slot 136 can extend at an angle to a distal portion 139 of the slot 136, for example the proximal portion 138 can form an S-shape with the distal portion 139. Thus, where the guide 120 is seated in the lumen 132 such that the proximal portion 126 of the guide 120 extends through the slot 136, the guide 120 can be oriented in one of two different directions. First, where the proximal portion 126 of the guide 120 extends through the proximal portion 138 of the slot 136, as shown in FIGS. 7A-7C, the distal portion 122 of the guide 120 can extend in a first direction. Second, where the proximal portion 126 of the guide 120 extends through the distal portion 139 of the slot 136, the distal portion 122 of the guide 120 can extend in a second direction, e.g., approximately ninety degrees from the first direction. A person skilled in the art will recognize a number of other configurations that the slot 136 can form without departing from the spirit of the present disclosure.

As mentioned above, in some embodiments at least the proximal portion 138 of the slot 136 can be configured to remain outside the patient's body when at least a distal portion of the sleeve 130 is inserted into the patient's body. In this way, a user can access the proximal portion 126 of the guide 120 to manipulate the distal portion 122 of the guide 120 while the distal portion 122 is within the patient's body, e.g., to move the distal portion 122 between the first and second directions.

In some embodiments, a handle 150 can be attached to a proximal end of the sleeve 130, for instance to facilitate insertion of the sleeve 130 into a patient's body. The handle 150 can be attached to the sleeve 130 either permanently, for instance by being integrally formed with the sleeve 130, or it can be removably attached to the sleeve 130, for instance by screws 152a, 152b. The handle 150 can be configured in a variety of ways to improve the user's ability to deliver and/or position one or more surgical devices through the sleeve 130. In the illustrated embodiment, the handle 150 is a generally elongate member tapered upward in the proximal direction and having a curved lip on a terminal, proximal end thereof to facilitate gripping of the handle 150.

The system 100 can further include a locking mechanism to fix the guide 120 in place with respect to the sleeve 130, similar to locking mechanisms described above. In some embodiments, the locking mechanism can be a part of the sleeve 130, e.g., a latch or slot formed on a wall of the lumen 132 and being configured to snap into engagement with the guide 120. By way of non-limiting example, the proximal portion 138 of the slot 136 can function as the locking mechanism where the proximal portion 138 has a smaller width than a width of the distal portion 139. In such embodiments, the guide 120 can first be inserted into the sleeve 130 such that the proximal portion 126 of the guide 120 extends through the distal portion 139 of the slot 136. The guide 120 can then be locked into place with respect to the sleeve 130 by sliding the guide 120 proximally and rotating the guide 120 until the proximal portion 126 of the guide 120 passes through the proximal portion 138 of the slot 136. The relative dimensions of the proximal portion 126 of the guide 120 and the proximal portion 138 of the slot 136 can be configured to provide for an interference fit therebetween. In still further embodiments, the locking mechanism can be a separate component that is configured to be inserted into the lumen 132, for example through the slot 136 or through a second slot, or it can be configured in any other number of ways provided for herein or otherwise known to those skilled in the art.

Any number, shape, and size of guides as described herein can be used to guide surgical devices into a bone. By way of non-limiting example, FIGS. 9A to 9F illustrate alternate embodiments of a distal portion of a guide as described herein. In each of the alternate embodiments, the distal portion is bent away from an intermediate portion by approximately a ninety degree angle, although it will be appreciated by a person skilled in the art that the distal portion can be bent away at any angle. The shape of the distal portion can be configured to align with a particular bony structure, e.g., the flat shape of the distal portion 22a of FIG. 9A can be configured to align with a substantially flat bone surface, the concave curved shape of the distal portion 22b of FIG. 9B can be configured to align with a convex bone surface, and the V-shape of the distal portion 22c of FIG. 9C can be configured to align with a sharp or pointy bone surface. In the embodiment illustrated in FIG. 9D, the distal portion 22d can have demarcations 23d thereon for measuring a distance from a bony structure to a target location in bone. In this way, a surgeon can adjust an offset of the guide 20 from the target location intraoperatively, e.g., using an endoscope to view the distal portion 22d. In the embodiment illustrated in FIG. 9E, the distal portion 22e has a bulbous portion 25e thereon for facilitating engagement with an edge and/or a concave surface of a bone. In the embodiment illustrated in FIG. 9F, the distal portion 22f has a hook shape, which can facilitate grasping one or more bony structures and/or accessing surfaces of a bony structure that are on an opposite side of the bony structure that is being operated on, i.e., it is capable of contacting structures that are not otherwise directly accessible to the surgeon. It will be appreciated by a person skilled in the art that the distal portion 22 can have any one or more surface features thereon that are configured to facilitate engagement with bone, e.g., the distal portion 22 can be made from a material having a gripping surface thereon that is configured to frictionally engage bone.

Any one or more of the guides described herein can be used in conjunction with one another to help guide surgical devices. For example, up to four guides—either the same or different from one another—could extend through the four radial passageways 43a, 43b, 43c, and 43d of the trocar 40, such that up to four guides can be locked in position in the sleeve 30 by the trocar 40 to thereby stabilize the sleeve 30 by bracing the sleeve 30 against up to four bony structures. The lateral offset of each of the guides can be the same or different from one another, and generally can be in a range of about 1 millimeter to 50 millimeters. In this way, a position and orientation of the sleeve 30 can be set with respect to multiple anatomical landmarks, which can be located at varying distances from the sleeve 30. The use of more than one guide can also enhance the stability of the sleeve 30 and/or can help to stabilize fractured bone that is contacted by distal portions of each of the guides.

In some embodiments, one or more guides can be included as part of a surgical kit for creating a stabilizing offset from one or more bony structures. The surgical kit can include any of the guides as described herein, for example the guides illustrated in FIGS. 2, 7A-7C, and 9A-9F. Each of the guides can be either the same or different from one another and can be customized to contact a particular bony structure. Similarly, each of the guides can have a lateral offset that is customized to stabilize the sleeve at a predetermined distance from each of the bony structures contacted by the guides. By way of non-limiting example, the surgical kit can be configured for use in a glenoid fixation procedure. The kit can include a first guide having a first lateral offset that is configured to contact the glenoid rim, and a second guide having a second lateral offset that is configured to contact, by way of non-limiting examples, the coracoid process, the clavicula, the femur condyle (femoral notch), the Eminencia, any allografts or autografts at the surgical site, etc. Generally, guides having various sizes, shapes, and configurations, e.g., distal tips, can be included as part of a surgical kit to allow for use with different patient anatomies, e.g., male vs. female and adult vs. child, and for use in different procedures, e.g., repairs near the glenoid rim vs. repairs elsewhere in the body.

The guide systems disclosed herein can generally be used to position surgical devices at a predetermined location and orientation with respect to one or more bones. In an exemplary embodiment, a guide system can be used to form a bone hole at a predetermined distance and at a predetermined orientation with respect to an edge of a bone.

In use, a sleeve of the guide system can be inserted into a body of a patient in accord with customary surgical procedures, which can include open surgery or minimally invasive surgery (e.g., using one or more access cannulae). A guide can be inserted into the sleeve such that a distal, bone-engaging portion of the guide extends distally beyond the sleeve and/or a proximal, stop portion of the guide abuts a proximal end of the sleeve. In some embodiments, where the guide is passed distally through the sleeve, the distal portion of the guide can be in a compressed configuration, in which the distal portion is substantially aligned with an intermediate portion of the guide. Once the distal portion of the guide advances beyond a distal end of the sleeve, it can assume an expanded configuration in which the distal portion is laterally offset from the intermediate portion by a predetermined distance. Using the laterally offset distal portion as a guide, a surgeon can locate a bony structure, such as an edge of a bone, and can thereby align the sleeve at a desired distance and/or at a desired orientation with respect to the edge of the bone. One or more direction indication features on the proximal portion of the guide can indicate a direction of the offset of the distal portion to help a surgeon brace the guide against the edge of the bone. For example, as in the illustrated embodiment of FIG. 2, the direction of the major axis $A_M$ of a loop formed by the proximal portion 26 of the guide 20 can correspond to a direction of offset of the distal portion 22 of the guide 20. Where the lateral offset of the distal portion can be adjusted intra-operatively, e.g., with the distal portion 22d of FIG. 9D, a surgeon can adjust the offset of the distal portion while viewing the distal portion with, e.g., an endoscope. In some embodiments, once the guide is oriented in the desired position, it can be locked in place within the sleeve by a locking mechanism, e.g., a trocar advanced distally into the sleeve. In still further embodiments, the above described process can be repeated with more than one guide, such that multiple guides extend through the sleeve and/or are locked with respect to the sleeve.

With the sleeve being oriented at the desired location and orientation, a surgeon can pass one or more surgical devices through the sleeve and/or through the trocar that can optionally be disposed within the sleeve. By way of non-limiting example, a K-wire can be advanced distally through a second passageway in the trocar, which can be disposed radially inward of the first passageway to thereby create additional offset of the K-wire from the distal portion of the guide. One or more depth indication features of the sleeve can indicate a depth that the K-wire is inserted into a surgical site to thereby ensure that the K-wire is advanced to a desired depth. The guide and/or the trocar can then be removed from the sleeve, leaving the K-wire in place to serve as a guide for one or more surgical devices, e.g., a bone implant. Surgical repair can then proceed according to accepted surgical techniques.

A person skilled in the art will appreciate that the above described steps of the exemplary surgical method can be performed in any order. By way of non-limiting example, the trocar can be inserted into the sleeve before the guide. Once the trocar is set within the sleeve, the guide can be advanced through a first passageway of the trocar by applying a distally-directed force to the guide. When the guide has been advanced to the point that distal portion of the guide extends beyond the distal end of the sleeve, the force can be removed and the guide can thus be locked in place within the trocar by interference fit within the first passageway. Additionally or alternatively, in some embodiments, the guide can be inserted into the patient's body before the sleeve. The sleeve can then slide over the guide through the incision and into the patient's body. In still further embodiments, the guide and the sleeve can be inserted approximately simultaneously into the patient's body, for instance by inserting them separately and then assembling them once inserted (provided the configuration of the system allows such a construction), or by assembling the guide with the sleeve before insertion into the patient's body.

Figure 10:
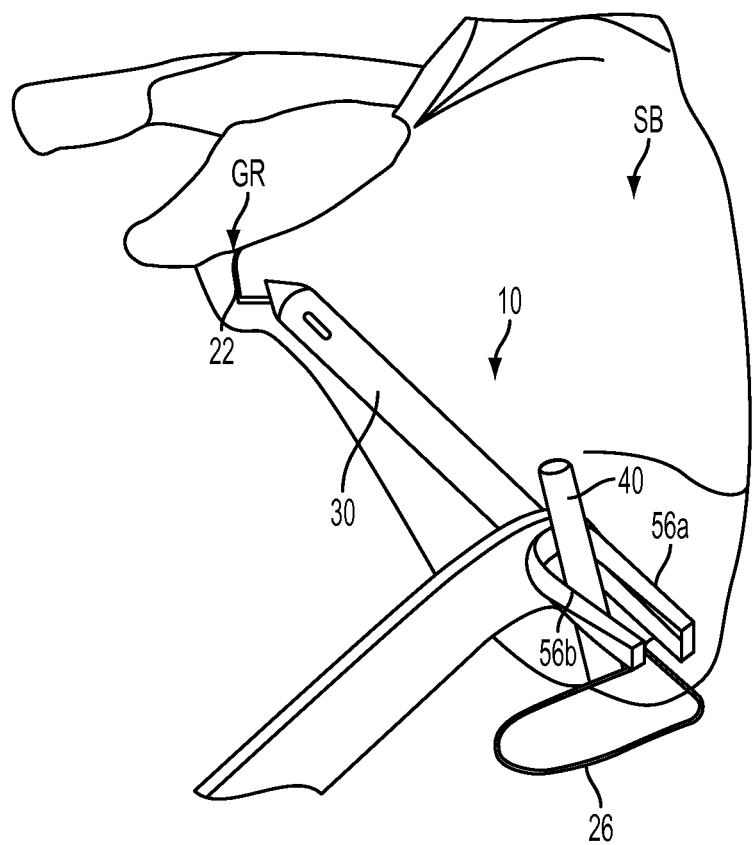
FIG. 10 is a perspective view of a step of a method for performing a glenoid fixation procedure using the guide system of FIG. 1.

The guide system can be used, for example, in an exemplary glenoid fixation procedure illustrated in FIG. 10, which is a simplified view of the anatomy of the shoulder blade SB with various soft tissue structures (including skin) removed for ease of illustration. Moreover, although cannulae for use in minimally surgical procedures are not illustrated (for ease of viewing), a person skilled in the art will understand that such devices can be used in a glenoid fixation procedure. FIG. 10 depicts the surgical system 10 fully assembled, with the guide 20 being locked in place by the trocar 40 within the sleeve 30. As shown, the distal portion 22 of the guide 20 is braced against the glenoid rim GR, thereby spacing a cross-sectional center of the sleeve 30 at a distance $D_G+D_T$ away from the edge of the glenoid rim. The proximal portion 26 indicates a direction of offset of the distal portion 22 to help the surgeon properly orient the system 10. Once the system 10 is assembled as shown in FIG. 10, a K-wire (not shown) can be inserted through the central passageway 45 of the trocar 40 to a desired depth, as indicated by demarcation lines 56a, 56b on the sleeve 30. Then, the guide 20 and/or the trocar 40 can be removed from the sleeve 30, leaving the K-wire in place to serve as a guide for a hole-forming instrument that forms a hole in the bone. An anchoring element such as a screw can then be inserted into the hole, and fixation can proceed according to accepted surgical techniques.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   inserting a sleeve through an opening in a patient's body and adjacent to a bone;
   inserting a guide through the opening in the patient's body;
   placing the guide in an inner lumen of the sleeve such that a distal tip of the guide extends distally beyond a distal-most end of the sleeve, the distal tip having a guide placement surface;
   rotating the guide such that its distal tip is disposed outside of a diameter defined by a diameter of the sleeve;
   inserting a trocar distally through the inner lumen to secure a fixed location of the guide with respect to the sleeve after the distal tip of the guide extends distally beyond the distal-most end of the sleeve;
   placing the guide placement surface against an edge of the bone such that the inner lumen of the sleeve is proximate to a bore formation location on the bone that is offset from the edge of the bone; and
   forming a bore in the bone at the bore formation location.

2. The surgical method of claim 1, wherein an outer surface of the trocar engages an outer surface of the guide to secure the fixed location of the guide with respect to the sleeve.

3. The surgical method of claim 2, further comprising inserting a K-wire distally through the trocar and into the bone.

4. The surgical method of claim 1, further comprising adjusting a location of the distal tip with respect to a main body of the guide after the guide has been passed distally through the sleeve.

5. The surgical method of claim 1, wherein the bone is a scapula and the edge of the bone is the glenoid rim.

6. The surgical method of claim 1, wherein the guide comprises an elongate body having an uncannulated interior throughout its length.

7. A surgical method, comprising:
   inserting a sleeve through an opening in a patient's body and adjacent to a bone;
   inserting a guide through the opening in the patient's body;
   placing the guide in an inner lumen of the sleeve such that a distal tip of the guide extends distally beyond a distal-most end of the sleeve, the distal tip having a guide placement surface;
   placing the guide placement surface against an outermost surface of the bone such that the inner lumen of the sleeve is proximate to a surgical site on the bone that is offset from the outermost surface of the bone; and
   passing one or more surgical devices through the sleeve, with at least one surgical device of the one or more surgical devices being passed outside of an outer surface of the guide.

8. The surgical method of claim 7, further comprising forming a bore in the bone at the surgical site.

9. The surgical method of claim 7, further comprising securing a fixed location of the guide with respect to the sleeve after the distal tip of the guide extends distally beyond the distal-most end of the sleeve.

10. The surgical method of claim 7, wherein the at least one surgical device of the one or more surgical devices is a trocar.

11. The surgical method of claim 10, further comprising engaging an outer surface of the guide with an outer surface of the trocar to secure a fixed location of the guide with respect to the sleeve.

12. The surgical method of claim 7, wherein the at least one surgical device of the one or more surgical devices is a K-wire.

13. The surgical method of claim 7, further comprising rotating the guide such that its distal tip is disposed outside of a diameter defined by a diameter of the sleeve.

14. The surgical method of claim 7, wherein the bone is a scapula and the outermost surface of the bone is the glenoid rim.

15. The surgical method of claim 7, wherein the guide comprises an elongate body having an uncannulated interior throughout its length.

16. A surgical method, comprising:
   inserting a sleeve through an opening in a patient's body and adjacent to a bone;
   inserting a guide into the sleeve, the guide having a distal portion that is biased into an expanded configuration, the distal portion being disposed in a compressed configuration when the distal portion is disposed in the sleeve;
   advancing the guide through the sleeve such that the distal portion extends distally beyond a distal-most end of the sleeve, causing the distal portion to move from the compressed configuration to the expanded configuration;
   securing a fixed location of the guide with respect to the sleeve after the distal portion of the guide extends distally beyond the distal-most end of the sleeve; and
   placing a guide placement surface of the distal portion of the guide against an edge of the bone such that the inner lumen of the sleeve is proximate to a surgical site on the bone that is offset from the edge of the bone.

17. The surgical method of claim 16, further comprising forming a bore in the bone at the surgical site.

18. The surgical method of claim 16, further comprising passing one or more surgical devices through the sleeve, with at least one surgical device of the one or more surgical devices being passed outside of an outer surface of the guide.

19. The surgical method of claim 18, wherein the at least one surgical device of the one or more surgical devices is a trocar.

20. The surgical method of claim 18, further comprising engaging an outer surface of the guide with an outer surface of the at least one surgical device of the one or more surgical devices to secure a fixed location of the guide with respect to the sleeve.

21. The surgical method of claim 18, wherein the at least one surgical device of the one or more surgical devices is a K-wire.

22. The surgical method of claim 16, wherein an effective width of the distal portion of the guide is less than or equal to a diameter of the guide when the distal portion is disposed in the compressed configuration, and the effective width of the distal portion of the guide is greater than a diameter of the guide when the distal portion is disposed in the expanded configuration.

23. The surgical method of claim 16, wherein placing the guide placement surface against an edge of the bone such that the inner lumen of the sleeve is proximate to a surgical site on the bone that is offset from the edge of the bone results in a direction indication feature located on a proximal portion of the guide that indicates a direction of offset of the guide placement surface.

24. The surgical method of claim 23, wherein the direction indication feature comprises a loop that is formed on a same side of the guide as the distal portion, the loop having a diameter that is larger than a diameter of the sleeve to prevent the loop from passing through the sleeve.

25. The surgical method of claim 16, wherein the bone is a scapula and the edge of the bone is the glenoid rim.

26. The surgical method of claim 16, wherein the guide comprises an elongate body having an uncannulated interior throughout its length.

* * * * *